US00PP30654P3

(12) United States Plant Patent
Danziger

(10) Patent No.: US PP30,654 P3
(45) Date of Patent: Jul. 2, 2019

(54) ***BIDENS* PLANT NAMED 'DBIDMECHAR'**

(50) Latin Name: *Bidens ferulifolia*
Varietal Denomination: DBIDMECHAR

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 77 days.

(21) Appl. No.: 15/731,182

(22) Filed: Apr. 28, 2017

(65) Prior Publication Data

US 2018/0317360 P1 Nov. 1, 2018

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC . A01H 5/02; A01H 5/025; A01H 5/00; A01H 6/14
See application file for complete search history.

(56) References Cited

U.S. PATENT DOCUMENTS

PP28,924 P3 * 1/2018 Psenner ..... A01H 5/02
Plt./410

OTHER PUBLICATIONS

BFG Supply Company GRO 'N SELL Quality Starter Plants 2016-2017 Annuals Program, retrieved on Aug. 30, 2018, retrieved from the Internet at https://www.bfgsupply.com/_CE/pagecontent/Documents/Plant%20Connection/Gro'n%20Sell%20Annuals.pdf, pp. 1-7, 24. (Year: 2018).*

Danziger Timeless Mega Charm, retrieved on Aug. 30, 2018, retrieved from the Internet at https://danzigeronline.com/variety/timeless-mega-charm/, 5 pp. (Year: 2018).*

* cited by examiner

*Primary Examiner* — June Hwu
(74) *Attorney, Agent, or Firm* — Cassandra Bright

(57) ABSTRACT

A new and distinct *Bidens* cultivar named 'DBIDMECHAR' is disclosed, characterized by a mounded growth habit. The new plant is very well branched and very compact. Flowers are extra-large, single, yellow and typically have eight petals. The new variety is a *Bidens*, normally produced as an outdoor garden or container plant.

2 Drawing Sheets

Figure 1:
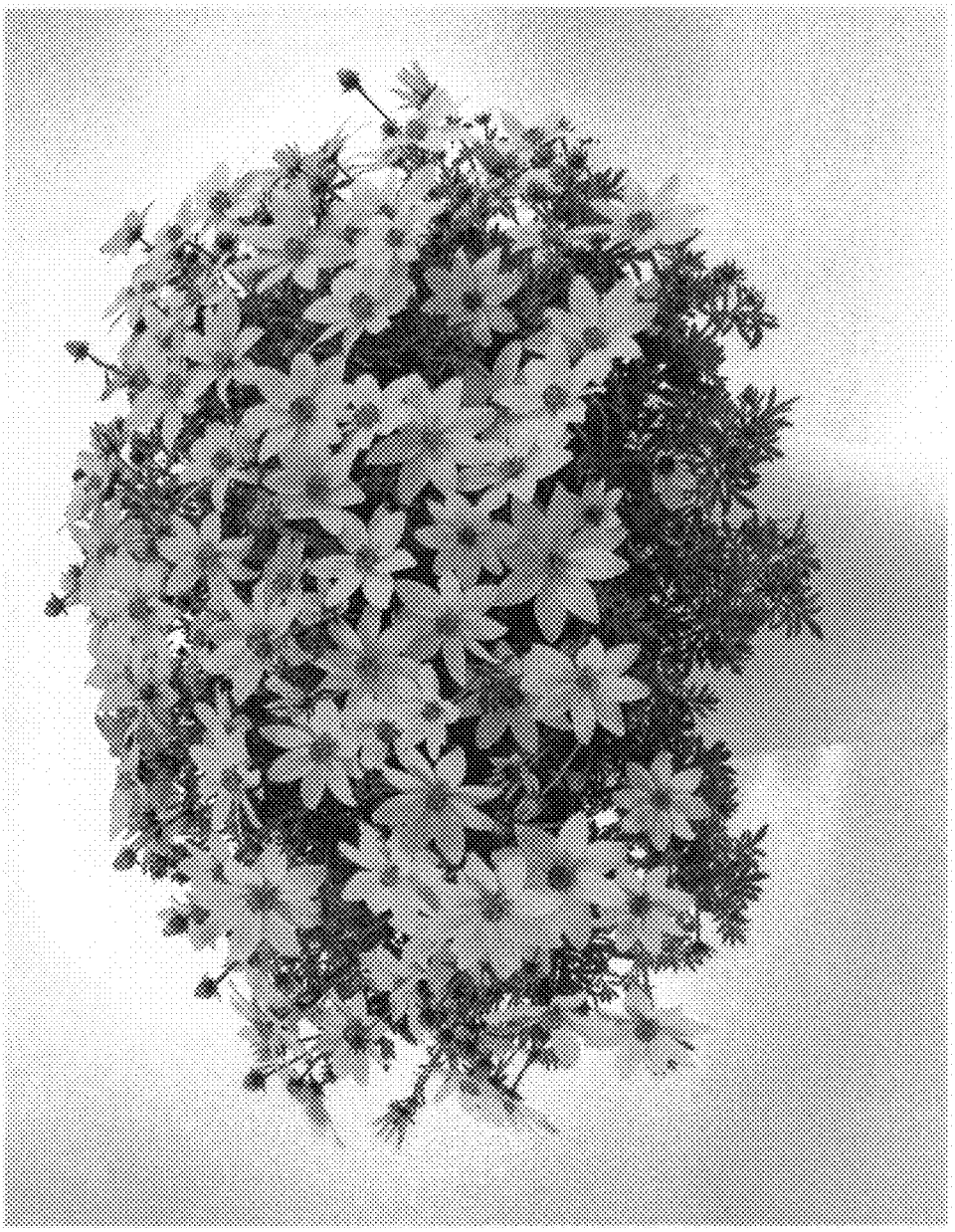

Latin name of the genus and species: *Bidens ferulifolia.*
Variety denomination: 'DBIDMECHAR'.

BACKGROUND OF THE INVENTION

The new *Bidens* cultivar is a product of a planned breeding program conducted by the inventor, Gavriel Danziger in Moshav Mishmar Hashiva, Israel. The open pollination resulting in this new variety was made during February of 2009.

The seed parent is the unpatented, propriety variety referred to as *Bidens* 'cv.14-1864'. The pollen parent is unknown as it was an open pollination breeding program. The new variety was discovered in December 2009 by the inventor in a group of seedlings resulting from the 2009 open pollination, in a greenhouse in Moshav Mishmar Hashiva, Israel.

Asexual reproduction of the new cultivar 'DBIDMECHAR' was first performed by terminal vegetative cuttings during December of 2009, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DBIDMECHAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBIDMECHAR' These characteristics in combination distinguish 'DBIDMECHAR' as a new and distinct *Bidens* cultivar:

1. Mounded growth habit.
2. Very well branched.
3. Very compact plants.
4. Extra-large, single, 8 petaled yellow flowers.

PARENT COMPARISON

Plants of the new cultivar 'DBIDMECHAR' are similar to plants of the seed parent in most horticultural characteristics, however, plants of the new cultivar 'DBIDMECHAR' differ in the following;

1. The new variety is mounded in plant habit, the seed parent has a semi-trailing growth habit.
2. The parent variety produces less branches per plant than the new variety.
3. The parent is a more vigorous plant than the new variety.
4. The seed parent has large, 5 petaled flowers, the new variety has extra-large flowers with 8 petals.

COMMERCIAL COMPARISON

Plants of the new cultivar 'DBIDMECHAR' can be compared to the commercial variety *Bidens* 'DANYEL9', U.S. Plant Pat. No. 20,968. These varieties are similar in most horticultural characteristics; however, 'DBIDMECHAR' differs in the following:

1. 'DANYEL9' has smaller flowers than the new variety.
2. 'DANYEL9' is less compact than the new variety.
3. 'DANYEL9' begins flowering earlier from a rooted cutting than the new variety.

Plants of the new cultivar 'DBIDMECHAR' can also be compared to the unpatented commercial variety *Bidens* 'DANYEL10'. These varieties are similar in most horticultural characteristics; however, 'DBIDMECHAR' differs in the following:

1. 'DANYEL10' has large, semi-double flowers whereas new variety has an extra-large, single flower.
2. 'DANYEL10' is less compact than the new variety.
3. 'DANYEL10' flowers earlier than the new variety.

BRIEF DESCRIPTION OF THE PHOTOGRAPHS

The accompanying photograph in FIG. 1 illustrates in full color a typical plant of 'DBIDMECHAR' grown in 13 cm pots outdoors in Moshav Mishmar Hashiva, Israel.

Figure 2:
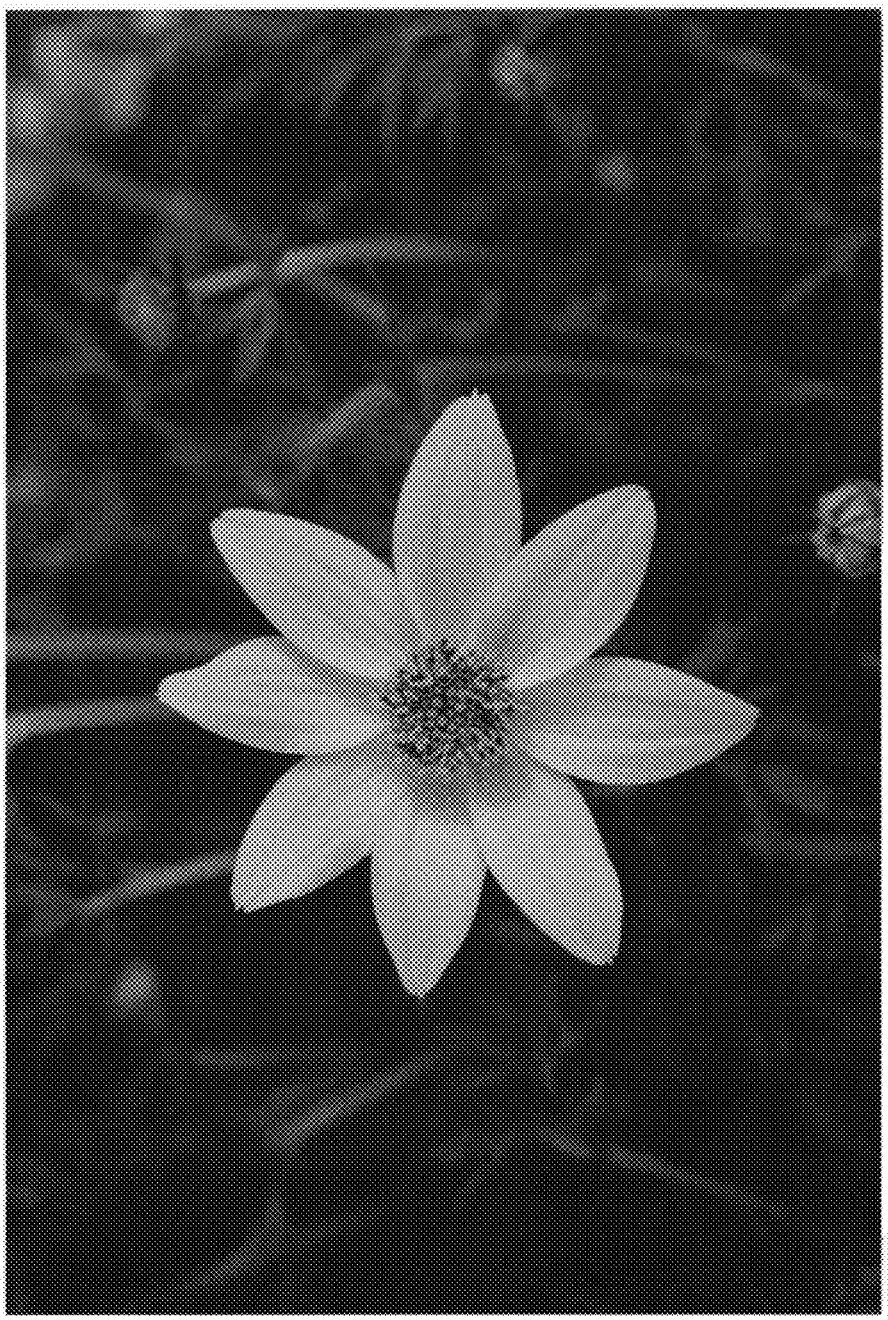

FIG. 2 illustrates in full color a close up view of a typical flower of 'DBIDMECHAR'. Age of the plant photographed is approximately 3 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color comparators are made to The Royal Horticultural Society Mini Colour Chart 2005 except where general terms of ordinary dictionary significance are used. The following observations and measurements describe 'DBIDMECHAR' plants grown in a greenhouse and outdoors in Moshav Mishmar Hashiva, Israel, under natural lighting. The plants were approximately 90 days old from a rooted cutting in a 13 cm pot. The growing temperature ranged from approximately 20° C. to 35° C. during the days, 17° C. to 23° C. during the nights. Measurements and numerical values represent averages of typical plant types.

Botanical classification: *Bidens ferulifolia* 'DBIDMECHAR'.

PROPAGATION

Time to initiate rooting: 10 to 14 days at approximately 20° C.

Root description: Fibrous. Medium brown in color, not accurately measured with R.H.S. chart.

PLANT

Growth habit: Mounded.
Height: Approximately 15 cm.
Plant spread: Approximately 30 cm.
Growth rate: Medium.
Branching characteristics: Well branched.
Length of lateral branches: Approximately 15 cm.
Diameter of lateral branches: Approximately 0.4 cm.
Texture of lateral branches: Pubescent.
Internode length: Approximately 2 cm.
Strength of stem: Good.
Color of lateral branches: Near RHS Yellow-Green 144 B.
Aspect/angle of branches: About 45°.
Number of leaves per lateral branch: Approximately 12.

FOLIAGE

Leaf:
- *Arrangement*.—Opposite.
- *Average length*.—Approximately 5 cm.
- *Average width*.—Approximately 3.5 cm.
- *Shape of blade*.—Bipinnate.
- *Apex*.—Acute.
- *Base*.—Cuneate.
- *Attachment*.—Petiolate, about 45° angle from stem.
- *Margin*.—Incised.
- *Texture of top surface*.—Slightly pubescent.
- *Texture of bottom surface*.—Slightly pubescent.
- *Appearance top surface*.—Matte.
- *Appearance bottom surface*.—Matte.
- *Leaf internode length*.—Approximately 0.8 cm.
- *Color*.—Young foliage upper side: Near RHS Green N137 A. Young foliage under side: Near RHS Yellow-Green 147 B. Mature foliage upper side: Near RHS Green N137 B. Mature foliage under side: Near RHS Yellow-Green 147 C.
- *Venation*.—Type: Pinnate. Venation color upper side: Near RHS Yellow-Green 147 B. Venation color under side: Near RHS Yellow-Green 147 B.

Leaflet:
- *Length*.—15-18 mm.
- *Width*.—8 mm.

Petiole:
- *Length*.—About 1.5 cm.
- *Diameter*.—About 0.2 cm.
- *Pubescence*.—Slightly pubescent.
- *Color*.—Near RHS Yellow-Green 147 B.

FLOWER

Bloom period: Year round in Beit Dagan, Israel.

Bud:
- *Bud shape*.—Rounded.
- *Bud length*.—Approximately 1.3 cm.
- *Bud diameter*.—Approximately 1.2 cm.
- *Bud color*.—Near RHS Yellow 12 A.

Inflorescence: Not relevant. Axillary, solitary flower.
- *Form*.—Not relevant.

Flower:
- *Diameter of entire flower*.—Approximately 5.5 cm.
- *Depth of flower*.—Approximately 1 cm.
- *Width of disc*.—Approximately 1.1 cm.
- *Depth of disc*.—Approximately 0.7 cm.

Ray florets:
- *Number of ray florets*.—Avg. 8.
- *Length*.—Approximately 2.2 cm.

*Width*.—Approximately 1.2 cm.
*Apex shape*.—Notched.
*Margin*.—Entire.

Color:
*Ray florets*.—Upper surface at first opening: Near RHS Yellow-Orange 14 A. Upper surface at maturity: Near RHS Yellow 12 A. Upper surface at fading: Near RHS Yellow 12 B. Under surface at first opening: Near RHS Yellow-Orange 14 A. Under surface at maturity: Near RHS Yellow 12 A. Under surface at fading: Near RHS Yellow 12 B.
*Disc florets*.—Number of Disc Florets: About 100. Length: Approximately 0.9 cm. Width: Approximately 0.1 cm. Shape: Linear. Margin: Entire. At first opening: Near RHS Yellow-Orange 17 A. At maturity: Near RHS Yellow-Orange 17 B. At fading: Near RHS Yellow-Orange 17 B.

Fragrance: Slightly Sweet.

Phyllaries/involucral bracts:
*Number*.—Average range 8 to 12, most commonly 12.
*Sepal length*.—Approximately 0.5 cm.
*Sepal width*.—Approximately 0.2 cm.
*Sepal texture*.—Slightly pubescent.
*Apex shape*.—Acute.
*Margin*.—Entire.
*Color*.—Near RHS Yellow-Green 147 A.

Peduncle: Not relevant.
*Pedicel length*.—Approximately 4.0 cm.
*Pedicel diameter*.—Approximately 0.2 cm.
*Angle*.—Approximately 45°.
*Color*.—Near RHS Yellow-Green 148 A.
*Pedicel texture*.—Glabrous.

REPRODUCTIVE ORGANS

Disc florets:
Androecium:
*Stamens*.—5.
*Anther shape*.—Linear.
*Anther length*.—Approximately 0.2 cm.
*Anther color*.—Near RHS Brown N 200 A.
*Pollen quantity*.—Sparse.

Gynoecium:
*Pistil number*.—1.
*Pistil shape*.—Linear.
*Pistil length*.—Approx. 0.5 cm.
*Style length*.—Approx. 0.2 cm.
*Style color*.—Near RHS Yellow-Orange 17 D.
*Stigma shape*.—Two-lobed.
*Stigma color*.—Near RHS Yellow-Orange 17 B.
*Ovary diameter*.—About 0.05 cm.
*Ovary color*.—Near RHS Yellow-Green 154 D.

Ray florets: Not present.

OTHER CHARACTERISTICS

Seeds and fruits:
*Shape*.—Needle-like.
*Color*.—RHS Black 202 A.
*Size*.—About 1 cm.

Disease/pest resistance: Neither resistance nor susceptibility to normal diseases and pests of *Bidens* has been observed.

Temperature tolerance: Temperature range: 5° C. to 40° C.

Drought tolerance: Not tolerant to drought.

What is claimed is:

1. A new and distinct cultivar of *Bidens* plant named 'DBIDMECHAR' as herein illustrated and described.

* * * * *